(12) United States Patent
Pott et al.

(10) Patent No.: US 7,208,173 B2
(45) Date of Patent: Apr. 24, 2007

(54) MIXED STRUCTURES RESULTING FROM THE INCORPORATION OF A BIOLOGICAL MACROMOLECULE, ESPECIALLY OF DNA, IN A LIQUID CRYSTAL PHASE OF AMPHIPHILES, AND VESICLES OBTAINED USING THESE STRUCTURES

(75) Inventors: Tanja Pott, Rennes (FR); René Laversanne, Pessac (FR); Didier Roux, Merignac (FR)

(73) Assignee: Capsulis, Pessac (FR)

( * ) Notice: Subject to any disclaimer, the term of this patent is extended or adjusted under 35 U.S.C. 154(b) by 583 days.

(21) Appl. No.: 10/148,897

(22) PCT Filed: Dec. 21, 2000

(86) PCT No.: PCT/FR00/03631

§ 371 (c)(1),
(2), (4) Date: Jun. 19, 2002

(87) PCT Pub. No.: WO01/45672

PCT Pub. Date: Jun. 28, 2001

(65) Prior Publication Data

US 2003/0003487 A1    Jan. 2, 2003

(30) Foreign Application Priority Data

Dec. 21, 1999  (FR) .................................. 99 16191

(51) Int. Cl.
*A61K 9/127*  (2006.01)
*A61K 51/00*  (2006.01)
*A61M 36/14*  (2006.01)

(52) U.S. Cl. ..................................... 424/450; 424/1.21
(58) Field of Classification Search ................ 424/450, 424/1.21
See application file for complete search history.

(56) References Cited

U.S. PATENT DOCUMENTS 5,679,355 A    10/1997  Alexander et al.
6,387,396 B2 *  5/2002  Mahy et al. ................. 424/450

FOREIGN PATENT DOCUMENTS

| FR | WO9518601 | * | 7/1995 |
| FR | WO9802144 | * | 1/1998 |
| GB | WO9823260 | * | 6/1998 |
| WO | 95/09610 | | 4/1995 |
| WO | 97/02114 | | 1/1997 |
| WO | 97/07784 | | 3/1997 |
| WO | 98/23260 | | 6/1998 |

* cited by examiner

*Primary Examiner*—Carlos A. Azpuru
*Assistant Examiner*—David Vanik
(74) *Attorney, Agent, or Firm*—Dennison, Schultz, Dougherty & MacDonald

(57) ABSTRACT

The invention relates to a structured mixed phase formed by the incorporation of a biological macromolecule into a liquid-crystal phase of amphiphiles, preferably a lamellar phase, wherein said biological macromolecule is present in said structured mixed phase in an amount of at least 5% by weight, based on the amphiphilic compounds constituting said liquid-crystal phase of amphiphiles, and wherein at least one of the two entities consisting of the biological macromolecules, on the one hand, and all the amphiphilic compounds, on the other, is of an uncharged nature.

The biological macromolecules incorporated into the structured mixed phases of the invention are preferably selected from polynucleotides, particularly DNA or RNA, proteins and polysaccharides.

The invention further relates to vesicles obtained by dispersion of the above structured mixed phases.

15 Claims, 3 Drawing Sheets

MIXED STRUCTURES RESULTING FROM THE INCORPORATION OF A BIOLOGICAL MACROMOLECULE, ESPECIALLY OF DNA, IN A LIQUID CRYSTAL PHASE OF AMPHIPHILES, AND VESICLES OBTAINED USING THESE STRUCTURES

This application is a filing under 35 USC 371 of PCT/FR00/03631, filed Dec. 21, 2000.

The present invention relates to novel products resulting from the incorporation of biological macromolecules, particularly DNA, into a liquid-crystal phase of amphiphiles, and to the processes for the preparation of these products.

Medicine has hitherto treated a disease by introducing an exogenous molecule to correct the dysfunction in question or at least to eliminate or limit its consequences. Unfortunately, the use of the active molecule employed in this strategy is most frequently accompanied by unwanted side effects which sometimes make the therapy unusable. Furthermore, some diseases associated with a genetic deficiency or defect cannot be treated by a "chemical" approach, either because the active molecule does not exist, or because it is destroyed before it can act, or because it would have to be administered in excessively large doses or over excessively long periods.

Gene therapy is a novel approach to tackling these inadequacies of conventional medicine. It consists in replacing a deficient gene or introducing a new gene in order to treat a pathological condition. With such a strategy, drugs are no longer administered but the organism is given the means to combat the disease or correct the deficiency which is causing the disease.

This strategy, made possible by the advances in molecular biology which have enabled genes of interest to be identified and synthesized, requires the ability to bring the useful gene to its cellular target, then cause it to enter the cell and finally cause it to be expressed. The gene has to be vectorized, i.e. introduced into a vector which will carry it through the various barriers protecting the organism and the cell from intrusion by foreign genetic material. The ideal vector must incorporate sufficient DNA (or RNA), protect it from the various forms of chemical and enzymatic attack encountered in vivo, be capable of reaching the desired cellular target preferentially, enter the cell, for example by endocytosis, protect the DNA from the very restricting conditions encountered in the endosome, bring the therapeutic gene to the nucleus and release it, allowing it to be expressed or, preferably, integrated into the genome of the cell.

Viruses are vectors of DNA (or RNA in the case of retroviruses) which satisfy most of these constraints perfectly. They have been studied very extensively as gene vectors for gene therapy and are the subject of numerous clinical trials. However, apart from the difficulties of handling them and producing them on a large scale, they have a major drawback, namely the suspicion which hangs over the possibility of their becoming virulent and causing uncontrollable new pathological conditions.

An important research is devoted to the development of synthetic vectors, which quite obviously carry no risk of virulence. Liposomes have been studied very extensively in this regard, but suffer from their intrinsic drawbacks: very low stability, very difficult preparation, very poor encapsulating ability and very poor or even non-existent ability to transfect the gene. A novel class of liposomes, prepared from cationic lipids, has been developed which partially overcomes the drawbacks of liposomes: better stability, simple preparation and significant transfection rate, albeit very low compared with viruses. However, these associations between cationic lipids and nucleotides are not liposomes in the strict sense, but rather complexes between the negatively charged nucleotide and the positively charged lipid (M. Schmutz et al., PNAS, 96, p. 12293 (1999)).

International patent application WO 98/02144 teaches that it is possible to integrate a nucleotide into multilamellar vesicles with an onion structure, protect it and transport it, thereby enabling its intracellular transfection.

More recently, patent FR 2 766 706 has described coiled multilamellar vesicles based on mixtures of anionic and cationic lipids, and their application to the transfection of nucleotides.

One of the obstacles to the use of liposomes for vectorizing DNA or genes is the impossibility of introducing a sufficient amount of nucleotides into the liposome. In the case of conventional as well as multilamellar liposomes, or vesicles with an onion structure, whose size is in the order of a micrometer, it is easy to imagine that the DNA molecule will have difficulties in becoming incorporated since its size is of the same order of magnitude. There is therefore a need to compact the molecule so that it adopts a folded conformation, giving it an apparent size compatible with encapsulation in these lipid vesicles.

As DNA is negatively charged, this compaction is effected in nature by the use of histones, namely cationic proteins which complex the DNA and produce very small particles (below 100 nm). Artificially, such molecules and other cationic molecules have been used for compacting DNA to enable it to be incorporated into lipid vesicles of the multilamellar vesicle or liposome type.

Work on the encapsulation of DNA by liposomes based on neutral lipids has been completely abandoned because of their poor encapsulating ability (<5%). Current work entails the use of cationic molecules of either surfactants or polymers to form complexes with DNA which are capable of protecting this molecule and allowing its transfection, at the same time affecting the compaction of the DNA molecule and its vectorization. The resulting particles are often referred to as cationic liposomes, although their method of preparation and their formulation are rather different from those of conventional liposomes.

Very recent works (cf., for example, I. Koltover et al., Science, 281, p. 78, 1998; J. O. Räder et al., Science, 275, p. 810, 1997; T. Salditt et al., Physical Review Letters, 79, p. 2582, 1997) have demonstrated that, in these complexes, the DNA forms phases of liquid-crystal symmetry which intercalate with the liquid-crystal phase formed by the cationic surfactants.

Several symmetries have been identified and X-ray diffraction experiments (synchrotron) clearly show the superposition of the diffraction patterns of each of the surfactant and DNA systems. Several cationic lipids have been used, leading to different symmetries of the liquid-crystal phase of the lipids. The work cited has demonstrated the importance of the role of the charge on the lipids and the role of the total charge on the complex, which can be positive or negative according to the ratio of cationic lipids to negative DNA. Also, it is suggested that these structures of intercalated liquid-crystal phases have an important part to play in the results obtained in transfection.

When they are introduced into a solvent, for example water, amphiphiles, which are commonly called surfactants, have the ability to auto-associate to form structured or organized phases. In particular, these phases include thermodynamically stable liquid-crystal phases, which have a partial crystallographic order (in one or two spatial directions), such as lamellar (or smectic) phases, which have a one-dimensional order, or hexagonal phases, which have a two-dimensional order. Phases which have a crystalline order, such as the cubic phase, also exist. These phases are often referred to as lyotropic because their appearance and stability depend on the concentration of the amphiphile in the solvent. They can also be thermotropic if their domain of existence depends on temperature. A description of these phases can be found in C. L. Khetrapol et al., Nuclear magnetic resonance studies in lyotropic liquid-crystals, 1975. The term 'structured phase' will be used hereafter to describe these phases in general terms, the exception being cases where the phase symmetry is explicitly indicated.

The inventors of the present invention have now discovered that it is possible to obtain structures of intercalated liquid-crystal phases of DNA and surfactants without the need to use cationic lipids. Contrary to what has been indicated in the literature, and totally surprisingly, the mixing of a liquid-crystal phase of neutral (e.g. zwitterionic) surfactant, for example a lamellar phase, with DNA can under certain conditions result in the formation of a mixed phase in which the surfactants form lamellar laminae stacked according to a smectic symmetry, with which the DNA molecules are intercalated, the latter themselves being arranged according to a liquid-crystal symmetry of the nematic type. Furthermore, and even more surprisingly, these results are obtained solely when a large amount of DNA is introduced into the lamellar phase, despite the fact that it is difficult to introduce a small amount of DNA into the lamellar phase with a good yield.

Pursuing their researches, the inventors of the present invention were able to establish that it was likewise possible to introduce different biological macromolecules, particularly nucleotide macromolecules, proteins or poly-saccharides, into structured phases without interaction of the electrostatic type between said macromolecules and the components of the structured phase, on condition, however, that a sufficient amount of these macromolecules was introduced into this structured phase.

Among the nucleotide macromolecules consisting of a concatenation of nucleotides and very often denoted by the generic term 'nucleotide', the present invention singles out oligonucleotides generally comprising from 10 to 30 and at most 100 base nucleotide groups, and polynucleotides comprising a larger number of base nucleotide groups, generally more than 100 and often more than 1000 base pairs. Even though it does not exclude the case of the oligonucleotides as defined above, the invention applies very particularly to the macromolecules of the polynucleotide type as defined above, particularly DNA.

The inventors were thus able to extend the results concerning the introduction of a concentrated phase of DNA into a structured phase to other biological polymers.

Thus the invention has made it possible to incorporate macromolecules into a structured phase formed of surfactant membranes, even though the characteristic size of these macromolecules is greater than the space between the amphiphilic lamellae of this surfactant phase. The macromolecule is introduced in a concentrated form into the novel structure of the invention and is therefore present at a high concentration in the final system formed. Thus the invention affords a structured mixture, hereafter called a structured mixed phase, formed by the incorporation, into a liquid-crystal phase of amphiphiles, of macromolecules whose characteristic size is greater than that of the liquid-crystal phase and whose proportion by weight is greater than 5%, based on the amphiphiles, without the intervention of an electrostatic interaction between the macromolecules and the amphiphiles.

It is always possible to define a characteristic size for the macromolecule, but it depends on the nature of this macromolecule. In general, it is possible to quote the radius of gyration, measured e.g. by means of static light scattering experiments. More precisely, in the case of proteins, the radius of gyration of the non-denatured protein will be taken since denaturation is generally accompanied by a variation in this radius. In the case of DNA, one takes the length of the non-condensed molecule, which is simply obtained by multiplying the characteristic length of one base pair (3.4 Å) by the number of base pairs.

It is also always possible to define a characteristic length for the liquid-crystal phase. In general, this will be the size of the one-dimensional or two-dimentional crystal lattice unit. This is related to the wave vector of the X-ray diffraction peaks. To give more concrete examples, this will be the periodicity of stacking of the lamellae in the case of the lamellar phase and the distance between tubes of surfactants in the case of the hexagonal phase.

The main interest of the invention is that it provides a means of forming concentrated structures of biological macromolecules without resorting (as is known to be the case in the prior art) to a form of incorporation in which the driving force is of an electrostatic nature. The invention therefore makes it possible to do away with the electrical charges which, in the prior art, disturb the biological activity of the complex formed and e.g. cause these complexes to adhere to the cell walls and be captured by plasma proteins.

Furthermore, as is apparent from the following description, the invention also makes it possible to prepare, from these mixed structures, multilamellar vesicles incorporating said macromolecules with degrees of encapsulation which are both high and controllable.

Thus, according to one of its essential characteristics, the invention relates to a structured mixed phase formed by the incorporation of a biological macromolecule into a liquid-crystal phase based on amphiphilic compounds, wherein said biological macromolecule is present in said structured mixed phase in an amount of at least 5% by weight, based on the amphiphilic compounds, and at least one of the two entities consisting of the biological macromolecule, on the one hand, and all the amphiphilic compounds, on the other, is of an uncharged nature.

In one particularly advantageous variant of the invention, the liquid-crystal phase of amphiphiles is a lamellar liquid-crystal phase.

The structured mixed phases of the present invention are mixtures in which the macromolecule intercalates, in a form of long-range order, with an amphiphilic phase, itself of long-range order, of the liquid-crystal type.

Liquid-crystal phase is understood as meaning a liquid-crystal phase obtained by mixing amphiphiles. Such a phase can generally be characterized on the one hand by its composition and on the other hand by a characteristic dimension, for example its smectic pitch, which is the distance between the lamellae of said phase in the case of the lamellar phase.

Uncharged amphiphile is understood as meaning a molecule of amphiphilic character but with a neutral overall charge. This includes not only non-ionic molecules but also amphoteric molecules, in which the positive and negative charges compensate one another within the same chemical structure and not through a mobile counterion.

As explained previously, it is in fact a total surprise to have succeeded in incorporating, into such a phase, biological macromolecules whose characteristic dimensions are far greater than those of the liquid-crystal phase, without involving electrostatic interactions.

In fact, the invention has made it possible to introduce substantial amounts of DNA or, more generally, nucleotide macromolecules or biological macromolecules into liquid-crystal phases based on uncharged surfactants, i.e. under conditions where, in contrast to the practices of the prior art, there is no interaction of an electrostatic type between the surfactants and the macromolecules.

It has also been possible, within the framework of the invention, to introduce uncharged macromolecules into liquid-crystal phases based on surfactants, i.e. once again without there being an electrostatic interaction to explain such an introduction, even though said macromolecules are considerably 'larger' than the distance between the lamellae of the liquid-crystal phase, and without appreciable deformation of said phase.

As explained previously, the biological macromolecules to which the present invention relates are essentially concatenations of nucleotides and particularly concatenations of the 'polynucleotide' type as defined above, proteins and polysaccharides.

Polynucleotides are macromolecules formed by a succession of the constituent bases of the genetic code, the principal polynucleotides being DNA and RNA. These are very large macromolecules whose length can reach 10 μm. By virtue of their chemical structure, polynucleotides always carry negative charges counterbalanced by cations.

Proteins are macromolecules formed by an assemblage of amino acids. Their molecular weight can range up to 200,000 Da or more and their radii of gyration can reach several hundred Angströms. Proteins can be cationic, neutral or anionic according to the nature and proportion of the different amino acids of which they are composed, but also according to the pH: the acid and amine groups protonate and deprotonate as a function of pH. However, the majority of proteins are anionic under normal pH conditions (approaching neutrality).

Polysaccharides are formed of saccharide chains ranging from a few to several million sugar units. The sizes can thus be extremely varied and can reach quasi-macroscopic dimensions. Polysaccharides can carry different electrical charges according to the nature of the chemical groups substituting the saccharide rings and according to pH.

Although the invention is of very particular interest in the case of biological macromolecules whose radius of gyration is very considerably greater than the distance between the amphiphilic lamellae of the liquid-crystal phase, it is nevertheless not limited to such macromolecules.

Any surfactant capable of forming a liquid-crystal phase, for example when mixed with water, can be used in the invention. In the preferred biological applications, care will be taken to use amphiphiles which are compatible with the application, particularly those which have a low toxicity and are well tolerated, especially at the cellular level. The invention is bound not to a particular surfactant or a particular family of surfactants but to an intrinsic property of the organized phases of surfactants. The amphiphiles which can be used are advantageously selected from the group comprising:

hydrogenated or non-hydrogenated glycerolipids, particularly phospholipids, ethoxylated or non-ethoxylated, linear or branched, saturated or mono- or polyunsaturated $C_6$ to $C_{30}$ fatty acids in the form of the acid or an alkali metal, alkaline earth metal or amine salt, ethoxylated or non-ethoxylated esters of sucrose, sorbitol, mannitol, glycerol, polyglycerol containing from 2 to 20 glycerol units, or glycol with the above fatty acids, mono-, di- or triglycerides or mixtures of glycerides of the above fatty acids, ethoxylated or non-ethoxylated, linear or branched, saturated or mono- or polyunsaturated $C_6$ to $C_{30}$ fatty alcohols, cholesterol and derivatives thereof, particularly charged or neutral cholesterol esters such as cholesterol sulfate, other derivatives with a sterol skeleton, particularly those of vegetable origin such as sitosterol or sigmasterol, ethoxylated or non-ethoxylated ethers of sucrose, sorbitol, mannitol, glycerol, polyglycerol containing from 2 to 20 glycerol units, or glycol with the above fatty alcohols, hydrogenated or non-hydrogenated, polyethoxylated vegetable oils, polyoxyethylene/polyoxypropylene block polymers (poloxamers), polyethylene glycol hydroxystearate, sphingolipids and sphingosine derivatives, polyalkyl glucosides, ceramides, polyethylene glycol/alkyl glycol copolymers, for example the copolymers of the ELFACOS family from AKZO NOBEL, polyethylene glycol/polyalkylene glycol ether di-block or tri-block copolymers, for example the copolymers of the ARLACELL family from ICI.

These amphiphiles or surfactants can be used by themselves or in a mixture. Some of these amphiphiles are capable on their own of forming a liquid-crystal phase, e.g. a lamellar phase, by being mixed with a polar solvent. Others are used solely in a mixture, in a lower proportion, to confer rigidity or elasticity properties on the liquid-crystal phase.

Those skilled in the art will know how to choose from these molecules those which are most suitable for forming a liquid-crystal phase and to check the formation of said liquid-crystal phase by optical microscopy. It will be noted that the majority of the surfactants mentioned above are uncharged and are therefore incapable of acting by electrostatic interaction in the condensation of the macromolecule which it is desired to insert into the liquid-crystal phase. Such uncharged surfactants are therefore suitable for the incorporation of charged macromolecules such as DNA. In the list given above, some surfactants do carry a charge, this being the case particularly of the fatty acid salts, some of the phospholipids or the sphingosine derivatives, which may be used for the incorporation of uncharged macromolecules into the mixed phases of the invention.

As explained previously, one of the essential characteristics of the invention is that it affords concentrated macromolecular structures without resorting to electrostatic forces. Thus, if the macromolecule is of ionic character, uncharged amphiphilic agents will be used according to the invention. However, a further possibility according to the invention is to introduce relatively small amounts of products of ionic character into the compositions of the invention, for example in order to confer particular properties on the mixed structure of the invention or on the vesicles obtained by dispersion of this mixed structure (as will be apparent from the following description). In this case a distinction will be drawn between the main surfactant, which does not need to have any kind of ionicity, and the optionally ionic additive added in order to modify the properties of the structure formed, for example properties of adhesion to the cell walls. This distinction is easy to make since the novel structure of the invention, obtained by the incorporation of a large amount of biological macromolecule into a liquid crystal phase, can be obtained in the absence of the additive, but obviously not in the absence of the main surfactant.

It is therefore important to note that it is the respective role of the main surfactant and the additive which distinguishes them rather than the notion of their relative amounts. The additive, which can itself be a surfactant or a polymer, for example, may be ionic, in which case it can either be included in the structure or be grafted or adsorbed on the surface. Thus the additive may confer e.g. a surface adhesion property, which is of value for favoring the capture of the mixture including the macromolecule by a cell.

The preferred method of preparing these novel structures is very similar to that used for multilamellar vesicles of surfactants.

In general, this process comprises the following steps:
preparation of a homogeneous mixture containing the amphiphilic compounds and the macromolecule, said macromolecule being present in proportions of at least 5% by weight, based on said amphiphilic compounds, and incorporation of an appropriate amount of aqueous or polar medium to form a liquid-crystal phase with said amphiphilic compounds.

The appropriate amount of aqueous medium may be checked by optical or polarization microscopy to demonstrate the formation of the liquid-crystal phase.

The value of 5% given above is a minimum value for obtaining the structured mixed phase of the invention. Those skilled in the art will readily understand that the optimum values of this ratio vary with the nature and dimensions of the macromolecule and with the nature of the amphiphilic agents used. In general, it has been found that the incorporation of the macromolecule into the liquid-crystal phase improves as the amount of macromolecule used increases. The limiting values which can be encountered are governed more by practical considerations, particularly the maximum concentrations of macromolecule which produce solutions or dispersions of sufficient fluidity to be handled, than by theoretical considerations. It can easily be imagined, however, that a 1/1 ratio of surfactant to macromolecule is a reasonable limit, albeit not an absolute one.

Thus, in the case of the preparation of a structured mixed phase according to the invention containing a macromolecule consisting of a concatenation of nucleotide groups, particularly DNA, the preferred method of preparation is very similar to that used for multilamellar vesicles of surfactants. It consists in preparing a lamellar phase from a surfactant or surfactant mixture and an aqueous phase. The aqueous phase contains at least a fairly concentrated solution of such a macromolecule, particularly a DNA or RNA molecule.

The weight ratio $\rho$ of amphiphiles to nucleotide macromolecules is between 20 and 1, preferably between 5 and 1 (indicating that there is 0.2 g to 1 g of nucleotide macromolecule per g of surfactants).

The mixture for preparing the lamellar phase can be made up in a single step, all the components being weighed separately and added together. In this case, to favor the homogeneity of the mixture, it is optionally possible to carry out one or more freeze/thaw cycles and/or one or more lyophilization/rehydration cycles.

If some components of the mixture are difficult to solubilize (for example cholesterol), another optional possibility is to use a solvent, for example an alcohol, a chlorinated solvent or a mixture of these solvents, in order to dissolve these components; a homogeneous mixture of these components is then obtained after evaporation and will give the liquid-crystal phase, preferably lamellar phase, on hydration.

The exact method of preparation is not critical to the success of the incorporation provided that the liquid-crystal phase, preferably lamellar phase, is concentrated and that there is no excess solvent (aqueous phase), and it is very possible to employ certain conventional methods used to increase the degree of encapsulation of a product in liposomes or other multilamellar vesicles of phospholipids or other uncharged amphiphiles. However, care will be taken to avoid any excess water or aqueous or polar solvent, which might lead directly to the formation of vesicles of the conventional liposome type. In fact, as indicated previously, the amount of water, aqueous medium or polar solvent shall correspond to the appropriate amount for forming a liquid-crystal phase, particularly a lamellar liquid-crystal phase.

The experiments performed by the inventors of the present invention have afforded a clear characterization of the novel structures formed on the basis of results obtained from X-ray diffraction of the phases obtained by mixing surfactants and macromolecules at different concentrations and thus plotting the phase diagram of the water/surfactant/macromolecule system, and on the basis of analysis of the electron density deduced from the intensities of the diffraction peaks.

The various results obtained, which are apparent from the description and the Examples below, are also given with reference to FIGS. 1 to 5 attached, in which:

FIG. 1A: $\rho=\infty$ (absence of DNA),

FIG. 1B: $\rho=80$,

FIG. 1C: $\rho=20$, and

FIG. 1D: $\rho=2$. In FIG. 1D the DNA inter-strand correlation peak is indicated by an arrow in the insert.

The results observed in the case of DNA are given below. This molecule was chosen for two reasons, firstly because it was genuinely impossible to encapsulate useful amounts of DNA in non-cationic microvesicles, and secondly because, from a demonstrative point of view, the very great length and the particular structure of DNA certainly make it the most difficult challenge to take up. Those skilled in the art will understand that if this method is capable of encapsulating large amounts of DNA, which is a particularly bulky molecule, generalization to other macromolecules like proteins or polysaccharides, whose behavior is more ordinary, does not present major difficulties.

The main experimental proof of incorporation of the nucleotide macromolecule into the lamellar phase is obtained by X-ray diffraction. In fact, like any liquid-crystal phase, the lamellar phase has a repeat period along the stacking axis and will give an X-ray diffraction signal, called a Bragg peak. The position of this diffraction peak (expressed as the diffraction angle or the wave vector q) depends directly on the repeat distance. Furthermore, the peak intensities are related to the electron density profile of the repeat unit.

The X-ray diffraction observations were made for different values of the lipid/DNA weight ratio ρ and for different values of the water concentration of the samples. Four diffraction graphs at constant hydration (50% of water) are given (cf. FIGS. 1A to 1D), in the absence of DNA, for ρ=80 (low DNA load), for ρ=20 (medium DNA load) and for ρ=2 (high DNA load).

Figure 1A:
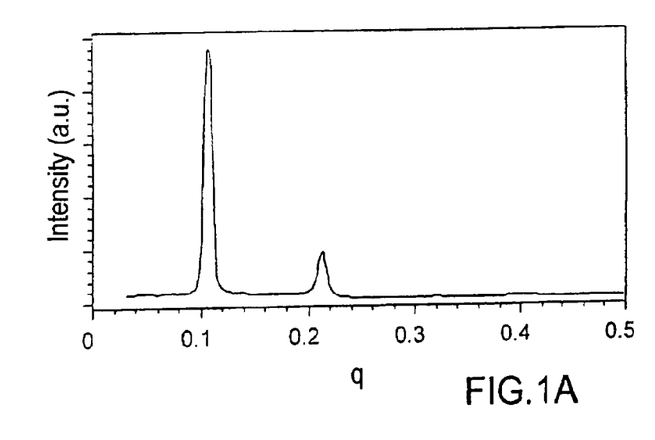
FIGS. 1A to 1D show the X-ray diffraction intensity (synchrotron) of the lamellar phases containing 50% of water as a function of the wave vector q ($q=4\pi \sin \theta/\lambda$) for different lipid/DNA weight ratios $\rho$.
Figure 1B:
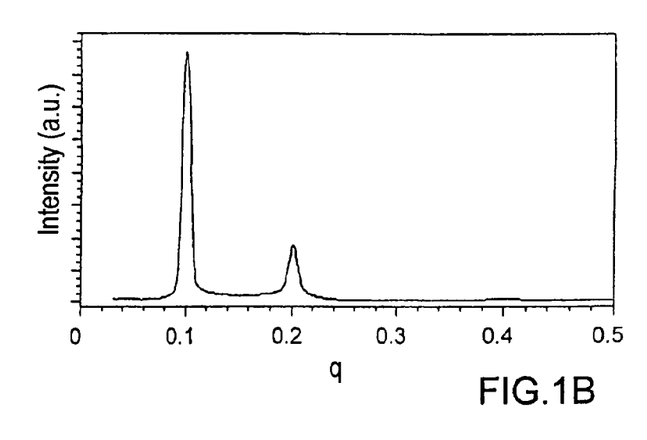
Figure 1C:
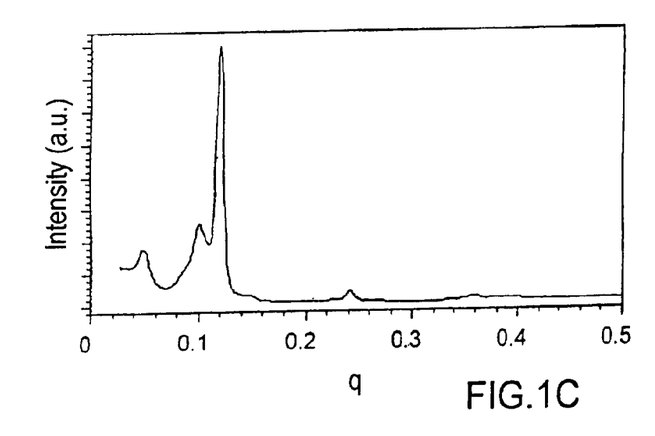

For the system in the absence of DNA or for small amounts of DNA, the Bragg peaks observed are characteristic of a lamellar phase (cf. FIGS. 1A and 1B). The repeat distance for ρ=80 (≅59 Å) is slightly reduced relative to the system in the absence of DNA (≅63 Å), probably because of a partial dehydration of the lamellar phase due to the presence of non-incorporated DNA.

For ρ=20, the co-existence of two diffraction systems is observed, revealing the co-existence of two lamellar phases (cf. FIG. 1C), the one being devoid of DNA with a smaller repeat distance (≅53 Å) than the lamellar phase in the absence of DNA, and the other being enriched in DNA with a very large increase in the repeat distance (≅129 Å).

Figure 1D:
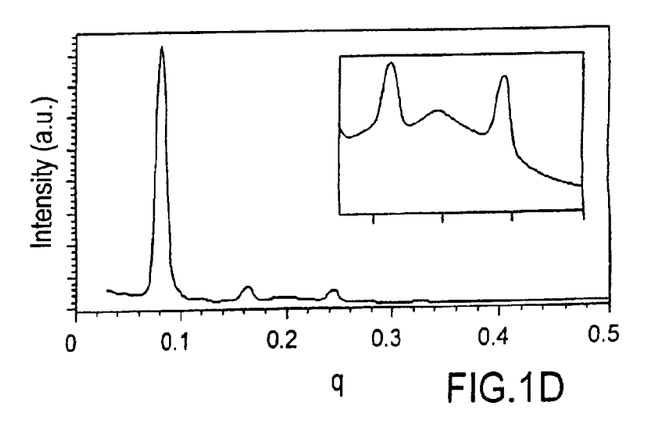

For ρ=2, the existence of a single lamellar system is observed with an increase in the repeat distance (≅77 Å) compared with the lamellar phase not containing DNA (cf. FIG. 1D). A DNA inter-strand correlation peak is also observed (≅32 Å). This peak shifts when the amount of DNA in the lamellar phase changes, showing that the DNA is indeed incorporated in the lamellar lipid phase in an ordered form. It was also observed that, when varying the water concentration of such a system, the two repeat distances, namely that of the lamellar phase and the DNA intermolecular correlation distance, varied in the same manner. From this it is deduced that, surprisingly, a DNA network intercalated with the layers of the lipid network exists at a high DNA concentration (the phenomenon is observable for ρ<6).

Figure 2A:
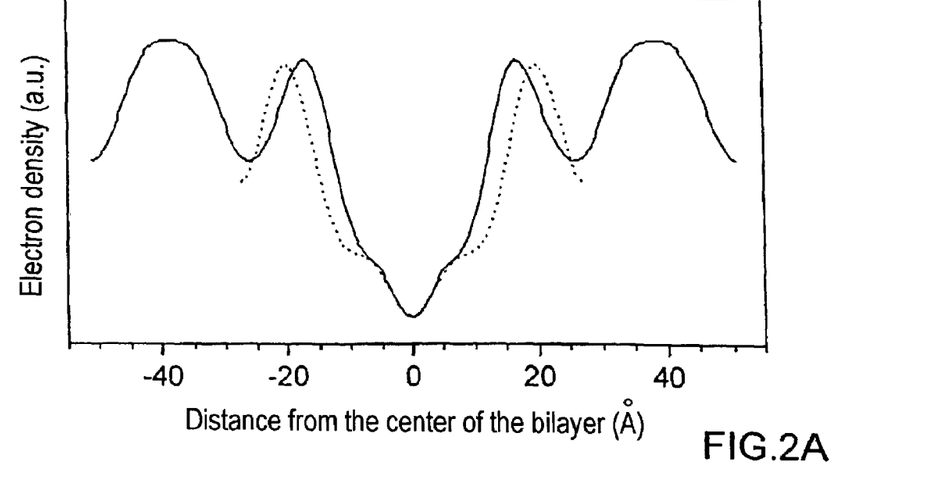
FIG. 2A shows the electron density profile along the stacking axis of the lipid layers for the lamellar phase for $\rho=2$ and $H_2O=47.4\%$ (continuous line). For comparison, the electron density profile of a lamellar phase in the absence of DNA is also shown (dotted line).
Figure 2B:
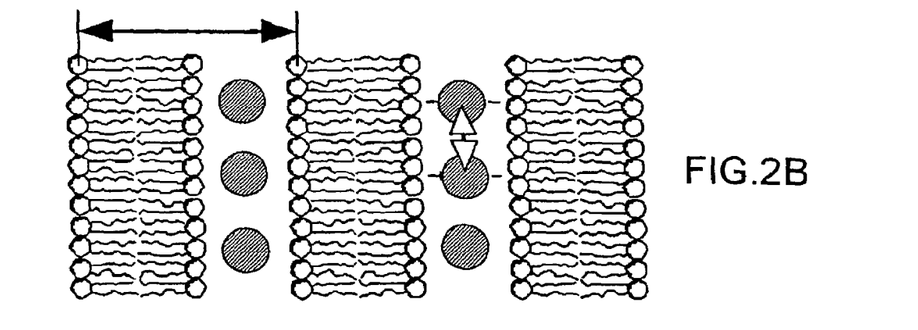
FIG. 2B is a diagrammatic representation of the lamellar phase containing the organized DNA ($L^c_\alpha$); the long horizontal arrow indicates the repeat distance of the lamellar phase (around 80 Å) and the short vertical arrow indicates the DNA inter-strand distance (30 to 40 Å).

Another proof of the existence of this mixed system of intercalated networks of lamellar lipid phase and organized DNA phase is deduced from analysis of the electron density on the basis of the diffraction peak intensities. The electron density profile of a lamellar lipid/DNA/water phase (ρ=2) along the stacking axis of the lipid layers is shown in FIG. 2. For comparison, the electron density profile of a lamellar phase in the absence of DNA is also shown as a dotted line in the Figure. The major difference between these two profiles is the presence of a hump of high electron density at about 40 Å from the center of the lipid bilayer, which has a width at half-height of about 10 Å. This is compatible with the presence of DNA molecules intercalated with the lipid bilayers in the aqueous phase. This lamellar phase containing organized DNA will hereafter be called $L^c_\alpha$.

These observations are wholly similar to those made with cationic lipids (cf. I. Koltover et al., Science, 281, p. 78, 1998; J. O. Räder et al., Science, 275, p. 810, 1997; T. Salditt et al., Physical Review Letters, 79, p. 2582, 1997), but, totally unexpectedly, this phenomenon is obtained for phases of uncharged surfactants.

This result is surprising because the explanations put forward by the authors of studies on the incorporation of DNA into lamellar phases of cationic lipids involved the presence of strong ionic interactions between the lipids and the nucleotide. In the case of the invention, such interactions do not exist and the explanation known to those skilled in the art is therefore invalid. Without constituting a proof or an explanation of the phenomenon observed, it can be proposed that, in the case of the invention, the thermodynamic stability of the structure (mixed network of lipids and DNA) obtained only at high DNA concentration might be related to the small loss of entropy of such a system in which the two subassemblies are ordered, compared with a less concentrated system where this entropy term would not be as effective.

The novel structures demonstrated within the framework of the present invention and described above are found to be particularly valuable by virtue of the fact that they can be converted, by dispersion, to multilamellar vesicles with an onion structure which incorporate said macromolecules within them at concentrations never observed hitherto.

Thus, according to another of its features, the invention relates to vesicles obtained from the mixed media of the invention by simple dispersion of said medium, and to a process for preparing these vesicles and particularly for varying the degree of encapsulation of the macromolecules within said vesicles.

The experiments performed by the inventors of the present invention have in fact made it possible clearly to demonstrate that the macromolecules are indeed present in the lamellar phase even after dispersion of the latter in an aqueous medium, i.e. under conditions where the phase $L^c_\alpha$ is thermodynamically unstable.

Furthermore, the experiments performed by the inventors of the present invention have made it possible to show how, by varying the ionic strength of the dispersion medium, it is possible to vary the degree of encapsulation of said macromolecule within said vesicles.

Results obtained with DNA are given below. As indicated previously, generalization to other biological macromolecules presents no difficulties since these macromolecules always behave more simply than DNA. The considerations of the influence of ionic strength on the variation in degree of encapsulation are directly applicable to these macromolecules, the phenomenon being associated more with the osmotic pressures generated by the differences in ionic strength and with their consequences on the integrity of the vesicles than with the influence of the ionic strength on the conformation of the macromolecule.

Experiments were also performed to verify that DNA is indeed present in the lamellar phase even after dispersion of the latter in an aqueous medium, i.e. under conditions where the phase $L^c_\alpha$ is thermodynamically unstable. It was shown that, in view of the very high concentration of DNA in the lamellar lipid phase and the substantial osmolarity which results, it is essential to disperse the lamellar phase containing the DNA in an aqueous medium of sufficient ionic strength. This was achieved using an aqueous buffer as dispersion medium. The result is given as the curve shown in FIG. 3, where the encapsulation yield (measured as the amount of DNA encapsulated inside, relative to the total amount of DNA incorporated in the formulation) is plotted as a function of the osmolarity of the dispersion medium. The unit of osmolarity used hereafter is the milliosmomol (mOsm), a unit commonly used in the field of biology. This unit has a linear relationship with the Pascal: 100 mOsm=$2.4777.10^5$ Pa.

It is observed that, for an osmolarity above ≅500 milliosmomol, the encapsulation yield is constant at around 70%, but it will also be noted that a good degree of encapsulation of about 60% is already attained at 300 mOsm (physiological medium).

We also demonstrated a surprising phenomenon. It is possible to disperse the vesicles of the invention at an osmolarity above that of the physiological medium in order to optimize the degree of encapsulation of DNA, and then to dilute them in a physiological medium without loss of encapsulated DNA. We further demonstrated that the DNA encapsulated in the vesicles according to the invention based on neutral lipids is actually protected against degradation by DNase and that these dispersions have a very good stability (the degree of encapsulation falling from about 70% to about 60% in one month).

More generally, the dispersions of vesicles of the invention can be obtained by a process comprising the following steps:
- dispersion in a medium of the same osmolarity as the internal medium, and
- modification of the osmolarity of the external medium by the addition of salt or water or by dialysis in order to attain the desired osmolarity.

Figure 4:
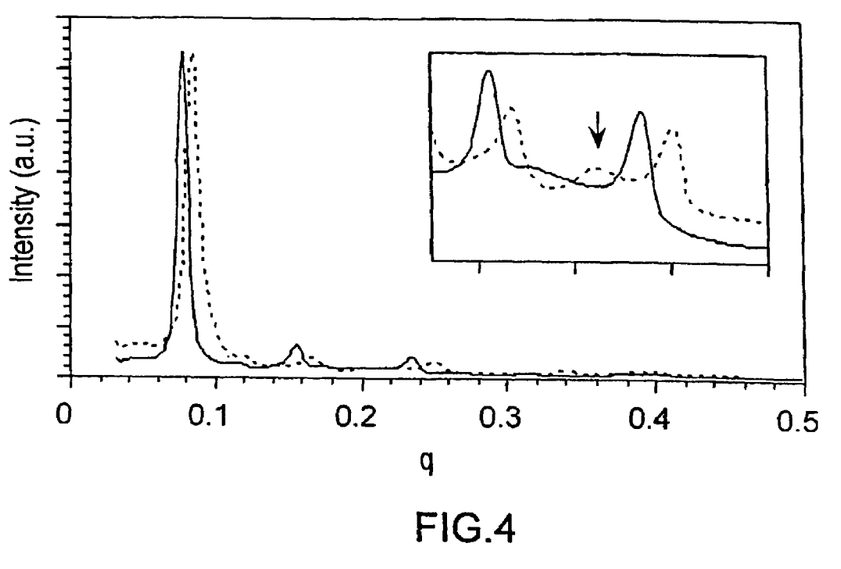
FIG. 4 shows the X-ray synchrotron diffraction profile of the vesicles obtained from the phase $L^c_\alpha$ for $\rho=2$ and $H_2O=50\%$, dispersed in a 603 mOsm medium (continuous line) and a 1457 mOsm medium (dotted line). The arrows in the insert indicate the DNA inter-strand correlation peaks.

The integrity of the phase $L^c_\alpha$ after dispersion in the form of vesicles was also verified by X-ray diffraction. The results are shown in FIG. 4. It is possible to note that the DNA inter-strand correlation peak is still observable. The repeat distance of the lipid bilayers and the DNA is modified according to the osmotic pressure of the dispersion medium. This clearly shows that the molecular arrangement is preserved even in the dispersion.

Figure 5:
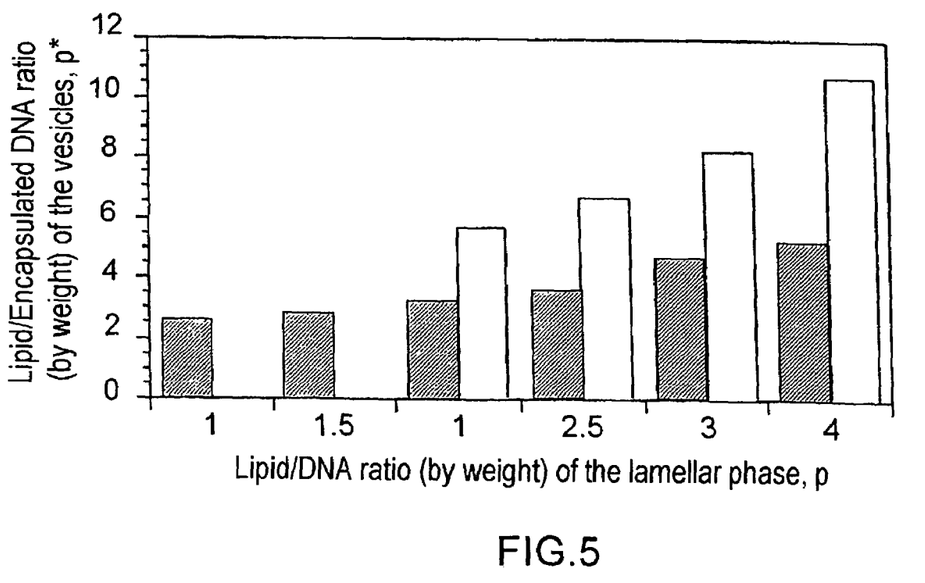
FIG. 5 shows the lipid/encapsulated DNA weight ratio ρ* of the vesicles containing DNA of ≅150 bp (dark gray) or a plasmid of 5581 bp (light gray), determined after dilution of the vesicles in PBS of 300 mOsm, as a function of the lipid/DNA weight ratio ρ of the lamellar phase.

The change in the lipid/encapsulated DNA weight ratio of the vesicles according to the invention dispersed in physiological medium, $\rho^*$, as a function of the lipid/DNA weight ratio of the phase $L^c_\alpha$ before dispersion, $\rho$, is shown for two types of DNA in FIG. 5. It is more astute to represent the encapsulation capacity by $\rho^*$ than by the percentage encapsulation because the former corresponds directly to the amount of DNA in the vector. For the short DNA (≅150 bp) and for the plasmid (5581 bp), $\rho^*$ decreases (the amount of DNA in the vector increases) with the decrease in $\rho$ of the phase $L^c_\alpha$. The encapsulation capacity of the vesicles of the invention based on neutral lipid is smaller for the large plasmid than for the short DNA, but $\rho^*$ values in the order of 6 are nevertheless attained, i.e. substantial amounts of plasmid are encapsulated.

The applications of this technique are very important in the field of gene vectorization for gene therapy. In fact, the ability to incorporate a large amount of nucleotide macromolecules with a very good encapsulation yield is an important condition of the success of such approaches. In addition, however, the fact that it is not necessary to use cationic lipids enables such systems to be used in vivo, where cationics are rapidly captured by the proteins and are hence ineffective. Furthermore, neutral lipids have a much lower cytotoxicity than cationic lipids.

These considerations of capture by the circulating proteins, adhesion to the cell walls, and cytotoxicity, are obviously independent of the nature of the macromolecule incorporated into the vesicle.

EXAMPLES

Product:

The following starting materials were used in the Examples:

| | |
|---|---|
| soya 1,2-diacylglycerophosphatidylcholine | (Avanti Polar Lipid), |
| lauryl alcohol ethoxylated with 4 ethylene oxides | (C12E4) (SEPPIC), |
| 1-monooleyl-rac-glycerol (monoolein) | (Sigma), |
| YOYO-1 iodide | (Molecular Probes), |
| type I DNase | (Amersham France), |
| highly polymerized calf thymus DNA | (Sigma), |
| plasmid pCMV LUCIFERASI | (Qiagen GmbH). |

The calf thymus DNA was treated with ultrasound to give double-stranded fragments of the persistence length of the DNA. These fragments were found by agarose gel electrophoresis to have a size of about 150 base pairs (bp).

The percentages are by weight in all the Examples.

Mixing of the Amphiphilic Components:

The various lamellar phases were prepared as follows:

To simplify the preparation, a stock mixture of the different surfactants used in the formulation can be prepared first. This stock mixture can be prepared directly either at room temperature or with slight heating to accelerate the mixing. It is also possible to dissolve the different surfactants in a solvent (for example alcohol and/or chlorinated solvent) in order to mix them in the correct proportions, and then to evaporate the solvent off under vacuum to give the stock mixture of surfactants. This method also allows the solution to be sterilized by filtration, if necessary.

The stock mixture can be stored at −18° C. for subsequent use.

Preparation of the Lamellar Phases Containing DNA:

The amount of DNA required to obtain the desired lipid/DNA weight ratio is added to the dry homogeneous mixture of the lipids. This is done most simply by adding the desired amount of DNA in aqueous solution. The system is mixed and left to stand in order to allow it to homogenize. The time required to reach equilibrium depends on the hydration and the DNA content of the system (a few days on average). The homogeneous lamellar phase can then be stored in the dark at −20° C. for several months without losing its characteristics and without the constituents undergoing chemical degradation.

Preparation of the Vesicles from the Phase $L^c_\alpha$:

Dispersion of the lamellar phase in a buffer of the desired osmolarity produces the vesicle phase. The vesicles can easily be dispersed by gentle agitation for a few hours. The homogeneity of the dispersion is checked meticulously by phase contrast microscopy.

If it is desired to improve the size homogeneity, it is also possible to shear the structured phase between two clean glass slides. The shearing is monitored by optical microscopy between crossed polarizers.

In the case of the phase $L^c_\alpha$ containing the plasmid, the integrity of the plasmid after shearing and dispersion was checked by agarose gel electrophoresis.

Measurement of the Osmotic Pressures:

The osmotic pressure inside the vesicles containing DNA was estimated from measurements of the osmotic pressure of the aqueous solutions of 150 bp DNA on a 13 DR-Autocal clinical osmometer. The osmotic pressure of the aqueous DNA solution changes non-linearly with the DNA concentration, which is the conventional behavior of macromolecules. The estimates show that the osmotic pressure of the phase $L^c_\alpha$ for $\rho=2$ and water=50% (by weight) is in the order of 500 milliosmomol, corresponding to a salinity of about 0.28 M. The osmotic pressure of the different buffers used was adjusted by adding NaCl and checked by experimental measurement.

Protection of the DNA in the Vesicles Against the Action of DNase:

Vesicles containing DNA and non-encapsulated control DNA were incubated with type I DNase in the presence of $Mg^{2+}$. Type I DNase is an endonuclease which catalyzes the degradation of single and double strands of DNA and produces terminal 5'-P oligonucleotides. It requires the presence of divalent cations in order to function. The degradation by DNase was stopped at different times by adding EDTA and the DNA was analyzed by gel electrophoresis. Even long after the control DNA has been completely destroyed, the encapsulated DNA shows no sign of degradation.

X-ray Diffraction:

For X-ray diffraction, the samples are transferred to 1 mm glass capillaries or to flat supports (irradiated thickness=1 mm) and sealed. The X-ray diffraction experiments were performed either on a rotating anode generator (CuKα, λ=1.5405 Å) or on a synchrotron (λ=1.0 Å, beamline ID2, ESRF, Grenoble) with a 2D detector and variable sample-detector distances (500 mm to 1000 mm).

After rearrangement, the exact positions of the peaks and their intensity were obtained by gaussian parameterization of the peaks after subtraction of the background. In cases where several peaks per phase were obtained, the repeat distances, d, were determined by a least squares parameterization of the slope of $(h^2+k^2+l^2)^{1/2}$ for the indices hkl (where l and k=0 for a lamellar phase) as a function of the reciprocal spacings.

The intensities, corresponding to the square of the structural factors, were corrected for the Lorentz factor and subjected to Blaurock normalization. The signs of the structural factors were obtained by the conventional expansion method. The electron density profiles of the phase $L^c_\alpha$ were then obtained by inverse Fourier transformation of the structural factors (cf. for example: Franks, N. P. & Levine, W. R., 1981, in Membrane Spectroscopy (Springer Verlag, Heidelberg, 437–487)).

X-ray diffraction experiments were performed on lamellar phases containing between 25 and 70% (by weight) of water, i.e. in the concentrated phase region, with ρ being between ∞ and 1, and on PC/C12E4 and PC/monoolein mixtures (95:5 by weight). The choice of co-surfactant does not seem to have any influence on the ternary phase diagram of the DNA/neutral lipid/water system. On the other hand, the repeat distances are slightly greater for the systems containing C12E4 and the swelling limit is shifted slightly towards the higher water concentrations. The DNA used to establish the phase diagram is treated with ultrasound beforehand and has a length of about 500 Å (≅150 bp).

Optically, excess water is observed for the lamellar phase at 50% of water or above. In the case of the samples containing DNA, the excess water is observed at between 55 and 60%, depending on the DNA content. Partial determination of the phase diagram by X-ray diffraction also makes it possible to distinguish between three systems: (i) the low DNA concentrations (large ρ), where the d values are lower than that of the lamellar phase without DNA (cf. FIG. 1B), (ii) the intermediate concentrations (medium ρ), where the co-existence of two lamellar phases in equilibrium is observed (cf. FIG. 1C), and (iii) the high DNA concentrations (small ρ), where a single lamellar phase is detected whose d is greater than that of the lamellar phase in the absence of DNA (cf. FIG. 1D). The decrease in d by a few Å in the case of a low DNA content (i) can be explained only if it is considered that at least part of the DNA is not incorporated into the lamellar phase and induces a partial dehydration of the latter. For the medium values of ρ (ii), the presence of a lamellar-lamellar biphase system resembles what has been observed in the case of mixed surfactant/polymer/water systems (Nallet, F. et al., 1994, J. Phys. II France, 4, 1477–1499). The DNA is found essentially in the phase of large d (about 110 to 130 Å); the phase of small d (around 50 Å) is devoid of DNA and slightly dehydrated. For $\rho \leq 6$ (iii), the only lamellar phase present is characterized by d values increased by 15 to 20 Å compared with the lamellar phase in the absence of DNA. This clearly demonstrates that the DNA is confined between the lipid lamellae. In contrast to the cationic lipid/DNA system, the confinement in this case is steric since there are no electrostatic interactions.

In addition to the peaks of the lamellar phase, a broad peak is observed at between q≅0.15 and 0.2 according to the composition of the lamellar phase (cf. insert of FIG. 1D). This peak does not exist for samples of ρ>6 and has been attributed to the DNA inter-strand correlation as observed for cationic lipid/DNA systems (J. O. Räder et al, Science, 275, p. 810, 1997; T. Salditt et al., Physical Review Letters, 79, p. 2582, 1997). The distance between DNA strands actually varies with ρ between ≈30 and 42 Å at constant hydration. These distances are characteristic of a nematic organization of DNA in water (Durand, D. et al., 1992, J. Phys. II France, 2, 1769–1783). We therefore have a lamellar phase $L^c_\alpha$ in which the DNA is intercalated with the smectic bilayers and has a 2D nematic organization (cf. also FIG. 1B). It is also observed that the distance between DNA strands decreases with the decrease in hydration at constant ρ. This is due to restriction of the wobbling of the DNA double strands when the interstitial space decreases.

X-ray diffraction was also carried out on vesicles containing encapsulated DNA and dispersed in buffer. For this purpose the vesicles were dispersed in a large excess of buffer and then concentrated. This dilution step followed by concentration eliminates virtually all of the non-encapsulated DNA. Results obtained with these preparations are shown in FIG. 4. The diffraction profile is characteristic of a lamellar phase and demonstrates the multilamellar character of the vesicles. As expected, the interlamellar distance d depends on the osmotic pressure of the dispersion buffer and increases by 15 to 20 Å compared with the vesicles not containing DNA. In addition, the presence of a DNA inter-strand correlation peak is easily detected, this peak shifting as a function of the amount of DNA in the vesicles and as a function of the osmotic pressure of the dispersion medium.

This is all in perfect agreement with what was found for the concentrated phases, thereby proving that the structure in the phase $L^c_\alpha$ is preserved in the vesicles.

X-ray diffraction experiments were also carried out on vesicles containing DNA in order to study the transfer from a hyperosmotic dispersion medium to a hypoosmotic medium (see below). In this case the vesicles were dispersed in a large excess of solvent at 900 mOsm (hyperosmotic). The solvent was then changed to lower the osmolarity to 300 mOsm (physiological medium; hypoosmotic for the phase $L^c_\alpha$). It is found that the lamellar structure remains intact even after transfer to the hypoosmotic medium. The d changes from about 78 Å at 900 mOsm to about 88 Å at 300 mOsm, i.e. the d values are still far greater than in the case of the vesicles not containing DNA ($\cong 63$ Å).

Also, electron density profiles of the phase $L^c_\alpha$ were reconstructed from the intensities of the Bragg peaks of the smectic arrangement. The profile given in FIG. 2A shows a hump of substantial electron density at about 40 Å from the center of the lipid bilayer and is consistent with the presence of DNA in the aqueous part of the lamellar phase.

Determination of the Degree of Encapsulation of DNA in the Vesicles:

The degree of encapsulation was determined by spectrofluorimetry using YOYO as the fluorophore ($\lambda_{ex}$=491 nm, $\lambda_{em}$=509 nm). Unless indicated otherwise, the results indicated below were obtained with DNA of $\cong$150 bp, treated with ultrasound.

The non-encapsulated DNA is measured by adding YOYO to aqueous dispersions of the vesicles ($I_D$). The total DNA is determined after destruction of the vesicles with Triton ($I_T$). The degree of encapsulation is obtained as follows: %=100·($I_T$-$I_D$)/($I_T$-$I_0$), where $I_0$=intensity of YOYO by itself. Conversion to the lipid/encapsulated DNA weight ratio is effected as follows: $\rho$*=100·$\rho$/degree of encapsulation.

Figure 3:
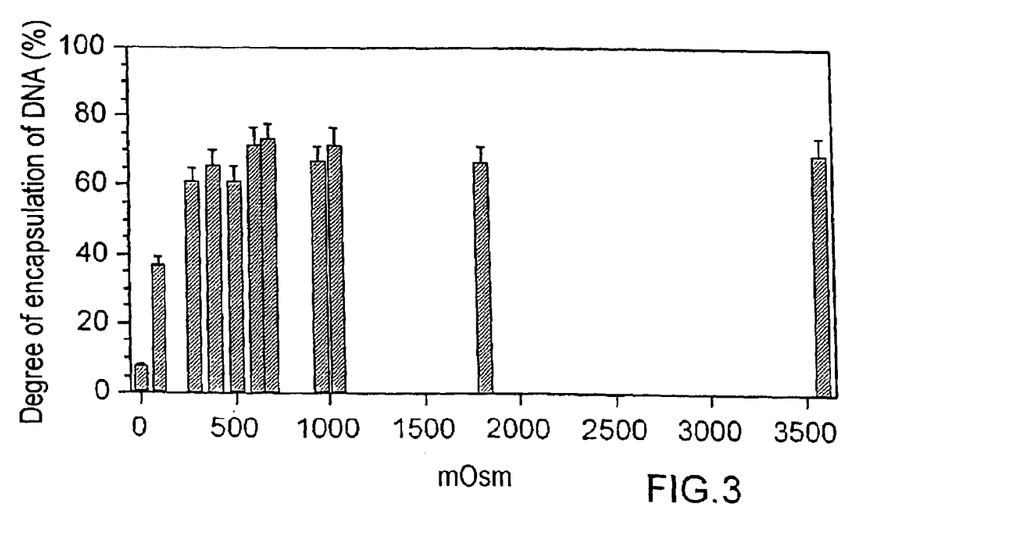
FIG. 3 shows the degree of encapsulation (measured as the amount of DNA encapsulated inside, relative to the total amount of DNA incorporated in the formulation) of the vesicles obtained from the phase $L^c_\alpha$ for $\rho=2$, plotted as a function of the osmolarity (expressed in milliosmomol) of the dispersion medium.

The degree of encapsulation of DNA in the vesicles was measured as a function of the osmotic pressure of the buffer. For this purpose the vesicles were prepared from a phase $L^c_\alpha$ at $\rho$=2 and at 55% hydration. The osmotic pressure inside the vesicles was estimated to be in the order of 500 mOsm. FIG. 3 shows that the degree of encapsulation increases gradually up to osmotic pressures of about 600 mOsm and remains constant for higher osmotic pressures, demonstrating the importance of the osmotic pressure for optimizing the degree of encapsulation. These results also suggest that the osmotic pressure inside the vesicles is probably slightly higher than the estimates obtained from the aqueous DNA solutions. This is probably due to the presence of salts in the phospholipid of natural origin.

It will nevertheless be noted that the optimum degree of encapsulation of DNA occurs at osmotic pressures above those of the physiological medium (300 mOsm). We therefore subsequently studied dilution of the vesicles (phase $L^c_\alpha$: $\rho$=2, 55% of water) prepared in a hyperosmotic medium (900 mOsm) in a 300 mOsm medium, hypoosmotic for the phase $L^c_\alpha$. In this case it is observed, totally surprisingly, that the degree of encapsulation does not fall to that of the vesicles prepared at 300 mOsm, but remains identical to that obtained at 900 mOsm. It is therefore possible to prepare vesicles containing DNA at high osmotic pressure and to dilute them in a physiological medium at the time of application without loss of encapsulated DNA.

A study of the stability of these DNA vectors as a function of time shows that the best stability is obtained in a hyperosmotic medium, where only a slight drop in the degree of encapsulation is observed, from $\cong$70 to $\cong$60%, over 30 days.

To study optimization as a function of the composition of the phase $L^c_\alpha$ used to produce the vesicles, the vectors were prepared in a hyperosmotic buffer and the degree of encapsulation was measured after they had been diluted in a physiological buffer.

When the water content of the phase $L^c_\alpha$ is varied between 40 and 70% at a constant $\rho$ of 2, the maximum degree of encapsulation is found at a hydration corresponding to the swelling limit of the phase $L^c_\alpha$ (55% of water). For degrees of hydration above 55%, the drop in encapsulation is explained by the fact that the DNA, which is soluble in the solvent, partitions itself between the phase $L^c_\alpha$ and the excess solvent and is therefore present to an ever-decreasing extent inside the phase $L^c_\alpha$. Below 55% the decrease in the degree of encapsulation when the hydration drops is probably a result of the low hydration and the increase in viscosity, both factors being obstacles to vesicle production.

Maintaining a degree of hydration of 50%, which corresponds to maximum encapsulation, we studied the influence of $\rho$ of the phase $L^c_\alpha$ on the degree of encapsulation. The results show that, in general, encapsulation is facilitated by the abundance of lipids (70% for $\rho$=4 compared with 45% for $\rho$=1). It is nevertheless important to realize that this result in % of encapsulated DNA gives no indication of the change in the amount of DNA encapsulated. The results converted to the lipid/encapsulated DNA weight ratio $\rho$* are shown in FIG. 5, where it is seen that for $\rho$=4, despite a high degree of encapsulation (70%), the total amount of DNA in the vesicles is less than the amount encapsulated for $\rho$=1. As regards optimization of the encapsulation, two points of view therefore become apparent: (i) either a large amount of DNA is introduced (low $\rho$), in which case the amount encapsulated is large but a lot of DNA is also observed in the external medium, (ii) or a small amount of DNA is introduced (high $\rho$), in which case most of the DNA will be encapsulated but overall there will be less DNA in the vesicles.

The influence of $\rho$ of the lamellar phase was also studied for the vesicles containing plasmid. In this case the degrees of encapsulation remain approximately constant at around 40% between $\rho$=4 and 2, i.e. lower than for short DNA. Nevertheless, the conversion to $\rho$* as a function of $\rho$ shows that the two systems change in a comparable way (cf. FIG. 5). This result enables the conclusions drawn from the system containing 150 bp DNA to be applied to the plasmid.

The invention claimed is:

1. A structured mixed phase comprising a first liquid-crystal phase of nucleotide macromolecules and a second liquid-crystal phase of amphiphilic compounds, said first and second liquid-crystal phases being intercalculated and in a weight ratio of amphiphilic compounds to nucleotide macromolecules of between 20 and 1, and wherein at least one of said nucleotide macromolecules or amphiphilic compounds is of an uncharged nature.

2. A structured mixed phase according to claim 1 wherein said liquid-crystal phase of amphiphilic compounds is a lamellar liquid-crystal phase.

3. A structured mixed phase according to claim 2 wherein said nucleotide macromolecules have a radius of gyration greater than a distance between amphiphilic lamellae of said liquid-crystal phase.

4. A structured mixed phase according to claim 1 wherein said nucleotide macromolecules are olynucleotides.

5. A structured mixed phase according to claim 1 wherein said amphiphilic compounds are selected from the group consisting of:
- hydrogenated or non-hydrogenated glycerolipids,
- ethoxylated or non-ethoxylated, linear or branched, saturated or mono- or polyunsaturated $C_6$ to $C_{30}$ fatty acids in the form of the acid or an alkali metal, alkaline earth metal or amine salt,
- ethoxylated or non-ethoxylated esters of sucrose, sorbitol, mannitol, glycerol, polyglycerol containing from 2 to 20 glycerol units, or glycol with said fatty acids,
- mono-, di- or triglycerides or mixtures of glycerides of the fatty acids,
- ethoxylated or non-ethoxylated, linear or branched, saturated or mono- or polyunsaturated $C_6$ to $C_{30}$ fatty alcohols,
- cholesterol and derivatives thereof,
- derivatives with a sterol skeleton of vegetable origin,
- ethoxylated or non-ethoxylated ethers of sucrose, sorbitol, mannitol, glycerol, polyglycerol containing from 2 to 20 glycerol units, or glycol with said fatty alcohols,
- hydrogenated or non-hydrogenated, polyethoxylated vegetable oils,
- polyoxyethylene/polyoxypropylene block polymers,
- polyethylene glycol hydroxystearate,
- sphingolipids and sphingosine derivatives,
- polyalkyl glucosides,
- ceramides,
- polyethylene glycol/alkyl glycol copolymers, and
- polyethylene glycol/polyalkylene glycol ether di-block or tri-block copolymers.

6. A structured mixed phase according to claim 1 which also contains at least one additive for conferring a surface adhesion property on said structured mixed phase.

7. A structured mixed phase according to claim 6 wherein said additive is a surfactant or polymer.

8. A process for the preparation of a structured mixed phase according to claim 1 which comprises the steps of:
- preparing a homogeneous mixture containing the amphiphilic compounds and the nucleotide macromolecules, in a weight ratio of amhiphilic compounds to nucleotide macromolecules of between 20 and 1, and
- incorporating an appropriate amount of aqueous or polar medium to form a liquid-crystal phase of amphiphiles with said amphiphilic compounds.

9. A process for the preparation of vesicles which comprises a step for dispersion of a structured mixed phase as defined in claim 1.

10. Vesicles obtained by the dispersion of a structured mixed phase as defined in claim 1.

11. A dispersion of vesicles according to claim 10 wherein the medium in which said vesicles are dispersed has a different osmolarity from that of the internal medium of the structured mixed phase of amphophiles.

12. A process for the preparation of a dispersion according to claim 11 which comprises the steps of:
- dispersing in a medium of the same osmolarity as the internal medium, and
- modifying the osmolarity of the external medium by the addition of salt or water or by dialysis in order to attain the desired osmolarity.

13. A structured mixed phase according to claim 4 wherein said polynucleotide is DNA.

14. A structured mixed phase according to claim 5 wherein said glycerolipids are phospholipids.

15. A structured mixed phase according to claim 1 wherein said ratio is between 5 and 1.

* * * * *